United States Patent
Overton et al.

(10) Patent No.: US 11,215,597 B2
(45) Date of Patent: Jan. 4, 2022

(54) FORESTRY MANAGEMENT TOOL FOR ASSESSING RISK OF CATASTROPHIC TREE FAILURE DUE TO WEATHER EVENTS

(71) Applicant: AGERPOINT, INC., New Smyrna Beach, FL (US)

(72) Inventors: Alan Overton, Daytona Beach, FL (US); Tyler Mullenbach, Daytona Beach, FL (US); Karl Steddon, New Smyrna Beach, FL (US); K. Thomas McPeek, New Smyrna Beach, FL (US)

(73) Assignee: AGERPOINT, INC., New Smyrna Beach, FL (US)

( * ) Notice: Subject to any disclaimer, the term of this patent is extended or adjusted under 35 U.S.C. 154(b) by 0 days.

(21) Appl. No.: 16/603,159

(22) PCT Filed: Apr. 11, 2018

(86) PCT No.: PCT/US2018/027199
§ 371 (c)(1),
(2) Date: Oct. 4, 2019

(87) PCT Pub. No.: WO2018/191442
PCT Pub. Date: Oct. 18, 2018

(65) Prior Publication Data
US 2020/0033312 A1 Jan. 30, 2020

Related U.S. Application Data

(60) Provisional application No. 62/484,266, filed on Apr. 11, 2017.

(51) Int. Cl.
*G01N 33/00* (2006.01)
*G01M 5/00* (2006.01)
(Continued)

(52) U.S. Cl.
CPC ...... *G01N 33/0098* (2013.01); *G01M 5/0058* (2013.01); *G01M 5/0091* (2013.01);
(Continued)

(58) Field of Classification Search
CPC ............ G01N 33/0098; G01M 5/0058; G01M 5/0091; G06K 9/6201; G06K 9/0063;
(Continued)

(56) References Cited

U.S. PATENT DOCUMENTS 5,652,717 A   7/1997  Miller et al.
6,756,789 B1  6/2004  Parker et al.
(Continued)

FOREIGN PATENT DOCUMENTS

CN   103018092   4/2013
CN   103903400   7/2014
(Continued)

OTHER PUBLICATIONS

Lindner, et al., Climate change impacts, adaptive capacity, and vulnerability of European forest ecosystems, Forest Ecology and Management 2010, 259, 698-709.
(Continued)

*Primary Examiner* — Amandeep Saini
(74) *Attorney, Agent, or Firm* — Bryan Cave Leighton Paisner, LLP

(57) ABSTRACT

Systems, apparatuses and methods for determining a risk of catastrophic failure for a tree based on a mechanistic model of physical characteristics of the tree are described. The systems, apparatuses and methods include a mobile sensing platform comprising one or more sensors for obtaining data, a transport vehicle configured to transport the mobile sensing platform, a positioning sensor configured to precisely calculate geographic coordinates of the positioning sensor and the location of the positioning sensor relative to a
(Continued)

reference object as positioning data, and a processor configured to fuse the imaging data and the positioning data in order to determine conditions for catastrophic tree failure.

22 Claims, 10 Drawing Sheets

(51) Int. Cl.
*G06K 9/62* (2006.01)
*G06T 7/00* (2017.01)
*G06T 7/60* (2017.01)

(52) U.S. Cl.
CPC .......... *G06K 9/6201* (2013.01); *G06T 7/0012* (2013.01); *G06T 7/60* (2013.01); *G06T 2207/10028* (2013.01); *G06T 2207/10036* (2013.01); *G06T 2207/30188* (2013.01)

(58) Field of Classification Search
CPC ............... G06T 7/0012; G06T 7/60; G06T 2207/10028; G06T 2207/10036; G06T 2207/30188
USPC ........................................................ 382/110
See application file for complete search history.

(56) References Cited

U.S. PATENT DOCUMENTS

| | | | |
|---|---|---|---|
| 6,773,552 B1 | 8/2004 | Albert et al. | |
| 6,889,551 B2 | 5/2005 | Andrews et al. | |
| 7,046,841 B1 | 5/2006 | Dow et al. | |
| 7,066,449 B1 | 6/2006 | Trefan et al. | |
| 7,215,420 B2 | 5/2007 | Gellerman et al. | |
| 7,215,430 B2 | 5/2007 | Kacyra et al. | |
| 7,231,087 B2 | 6/2007 | Huber | |
| 7,403,268 B2 | 7/2008 | England et al. | |
| 7,603,904 B2 | 10/2009 | Harris et al. | |
| 7,643,966 B2 | 1/2010 | Adachi et al. | |
| RE41,175 E | 3/2010 | Vashisth et al. | |
| 7,720,605 B2 | 5/2010 | Welty et al. | |
| 7,995,054 B2 | 8/2011 | Wheeler et al. | |
| 7,995,055 B1 | 8/2011 | Ma et al. | |
| 8,199,977 B2 | 6/2012 | Krishnaswamy et al. | |
| 8,208,689 B2 | 6/2012 | Savolainen et al. | |
| 8,229,718 B2 | 7/2012 | Heil et al. | |
| 8,275,547 B2 | 9/2012 | Rousselle et al. | |
| 8,295,554 B2 | 10/2012 | Francini et al. | |
| 8,300,896 B2 | 10/2012 | Kelle et al. | |
| 8,306,941 B2 | 11/2012 | Ma | |
| 8,396,284 B2 | 3/2013 | Wheeler et al. | |
| 8,412,492 B2 | 4/2013 | Chang et al. | |
| 8,467,992 B1 | 6/2013 | Doyle | |
| 8,483,478 B1 | 7/2013 | Medasani et al. | |
| 8,527,476 B2 | 9/2013 | Salemann | |
| 8,537,337 B2 | 9/2013 | Welty | |
| 8,559,680 B2 | 10/2013 | Schnorr et al. | |
| 8,594,438 B2 | 11/2013 | Hiebl | |
| 8,599,365 B2 | 12/2013 | Ma | |
| 8,599,367 B2 | 12/2013 | Canham | |
| 8,670,591 B2 | 3/2014 | Mendez-Rodriguez et al. | |
| 8,723,886 B2 | 5/2014 | Stroila | |
| 8,730,233 B2 | 5/2014 | McDaniel et al. | |
| 8,756,085 B1 | 6/2014 | Plummer et al. | |
| 8,760,285 B2 | 6/2014 | Billman et al. | |
| 8,767,190 B2 | 7/2014 | Hall | |
| 8,775,081 B2 | 7/2014 | Welty | |
| 8,775,220 B2 | 7/2014 | Maher | |
| 8,805,058 B2 | 8/2014 | Zebedin | |
| 8,811,748 B2 | 8/2014 | Morris | |
| 8,818,124 B1 | 8/2014 | Kia | |
| 8,825,392 B2 | 9/2014 | Stroila | |
| 8,861,840 B2 | 10/2014 | Bell et al. | |
| 8,861,841 B2 | 10/2014 | Bell et al. | |
| 8,879,828 B2 | 11/2014 | Bell et al. | |
| 8,885,925 B2 | 11/2014 | Cameron et al. | |
| 8,896,818 B2 | 11/2014 | Walsh et al. | |
| 8,924,210 B2 | 12/2014 | Basson et al. | |
| 9,047,688 B2 | 6/2015 | Lynch | |
| 9,063,544 B2 | 6/2015 | Vian et al. | |
| 9,069,061 B1 | 6/2015 | Harwit | |
| 9,103,671 B1 | 8/2015 | Breed et al. | |
| 9,129,435 B2 | 9/2015 | Lee et al. | |
| 9,161,019 B2 | 10/2015 | Millett | |
| 9,170,331 B2 | 10/2015 | Aimin | |
| 9,196,084 B2 | 11/2015 | Boardman et al. | |
| 9,198,363 B2 | 12/2015 | Vian et al. | |
| RE45,854 E | 1/2016 | Gittinger et al. | |
| 9,273,951 B2 | 3/2016 | Troxler | |
| 9,274,251 B2 | 3/2016 | Pasken et al. | |
| 9,275,267 B2 | 3/2016 | Verret | |
| 9,286,538 B1 | 3/2016 | Chen et al. | |
| 9,305,241 B2 | 4/2016 | Pope | |
| 9,322,646 B2 | 4/2016 | Pochiraju et al. | |
| 9,322,656 B2 | 4/2016 | Barnes et al. | |
| 9,329,271 B2 | 5/2016 | Ossig et al. | |
| 9,390,556 B2 | 7/2016 | Masry | |
| 9,424,672 B2 | 8/2016 | Zavodny et al. | |
| 2004/0130702 A1* | 7/2004 | Jupp | G01S 17/89 356/5.01 |
| 2007/0065857 A1* | 3/2007 | Glaser | G01N 21/3563 435/6.11 |
| 2010/0205219 A1* | 8/2010 | Rousselle | G06Q 10/10 707/797 |
| 2012/0114185 A1* | 5/2012 | Ram | G06Q 10/087 382/110 |
| 2014/0163772 A1* | 6/2014 | Vian | G05D 1/0094 701/2 |
| 2014/0257862 A1 | 9/2014 | Billman et al. | |
| 2015/0317740 A1 | 11/2015 | Emison et al. | |
| 2016/0069743 A1* | 3/2016 | McQuilkin | G01J 3/0205 356/416 |

FOREIGN PATENT DOCUMENTS

| | | |
|---|---|---|
| DE | 102014016247 | 5/2015 |
| MX | 2012003631 | 10/2012 |
| WO | 2016123201 | 8/2016 |

OTHER PUBLICATIONS

Dale, et al., Climate change and forest disturbances: Climate change can affect forests by altering the frequency, intensity, duration, and time of fire, drought, introduced species, insect and pathogen outbreaks, hurricanes, windstorms, ice storms, or landslides, Bioscience 2001, 51, 723.

Dale, et al., The interplay between climate change, forests, and disturbances, The Science of the Total Environment 2000, 262, 201-204.

Beach, et al., The influence of forest management on vulnerability of forests to severe weather, Rangeland Management 2010.

James, et al., Tree biomechanics literature review: Dynamics, Arboriculture and Urban Foresty 2014, 40, 1-15.

Moore, Differences in maximum resistive bending moments of Pinus radiata trees grown on a range of soil types, Forest Ecology and Management 2000, 135, 63-71.

Gilman, et al., Root system morphology influences lateral stability of Swietenia mahagoni, Arboriculture and Urban Forestry 2014, 40, 27-35.

Gardiner, et al., Comparison of two models for predicting the critical wind speeds required to damage coniferous trees, Ecological Modelling 200, 129, 1-23.

Rosell, et al., Obtaining the three-dimensional structure of tree orchards from remote 2D terrestrial LIDAR scanning, Agricultural and Forest Meteorology 2009, 149, 1505-1515.

Avalos, et al., Evaluation of failure criteria in branch members under torsion and bending moment, Arboriculture and Urban Forestry 2014, 40, 36-45.

Peltola, et al., Swaying of trees as caused by wind: analysis of field measurements, Silva Fennica 1993, 27, 113-126.

(56) References Cited

OTHER PUBLICATIONS

Gardiner, et al., Field and wind tunnel assessments of the implications of respacing and thinning for tree stability, Forestry 1997, 70, 233-252.
Mickovski et al., A decision support tool for windthrow hazard assessment and prevention, Forest Ecology and Management 216 (2005) 64-76.
Morgan et al., Structural analysis of tree trunks and branches: tapered cantilever beams subject to large deflections under complex loading, Tree Physiology 3 (1987) 365-374.
Ancelin et al., Development of an individual tree-based mechanical model to predict wind damage within forest stands, Forest Ecology and Management 203 (2004) 101-121.
Peltola, Model computations on wind flow and turning moment by wind for Scots pines along the margins of clear-cut areas, Forest Ecology and Management, Forest Ecology and Management 83 (1996) 203-215.
Schelhaas et al., Introducing tree interactions in wind damage simulation, Ecological Modelling 207 (2007) 197-209.
Rondeux et al., Review of indicators and field methods for monitoring biodiversity within national forest inventories. Core variable: Deadwood, Environmental Monitoring and Assessment (2010) 164: 617-630.
Peltola et al., A mechanistic model for assessing the risk of wind and snow damage to single trees and stands of Scots pine, Norway spruce, and birch, Canadian Journal of Forest Research (1999) 29: 647-661.
Lin, LiDAR: An important tool for next-generation phenotyping technology of high potential for plant phenomics, Computers and Electronics in Agriculture 119 (2015) 61-73.
Hildebrandt et al., From points to numbers: a database-driven approach to convert terrestrial LiDAR point clouds to tree volumes, European Journal of Forest Research (2012), 131: 1857-1867.
Peltola et al., Mechanical stability of Scots pine, Norway spruce and birch: an analysis of tree-pulling experiments in Finland, Forest Ecology and Management 135 (2000) 143-153.
Lin et al., Inspection and evaluation of decay damage in Japanese cedar trees through nondestructive techniques, Arboriculture & Urban Forestry (2016) 42(3): 201-212.
Monteith and Unsworth, Principles of Environmental Physics, Edward Arnold, London 1990.
Vollsinger et al., Wind tunnel measurements of crown streamlining and drag relationships for several hardwood species, Canadian Journal of Forest Research (2005) 35: 1238-1249.

\* cited by examiner

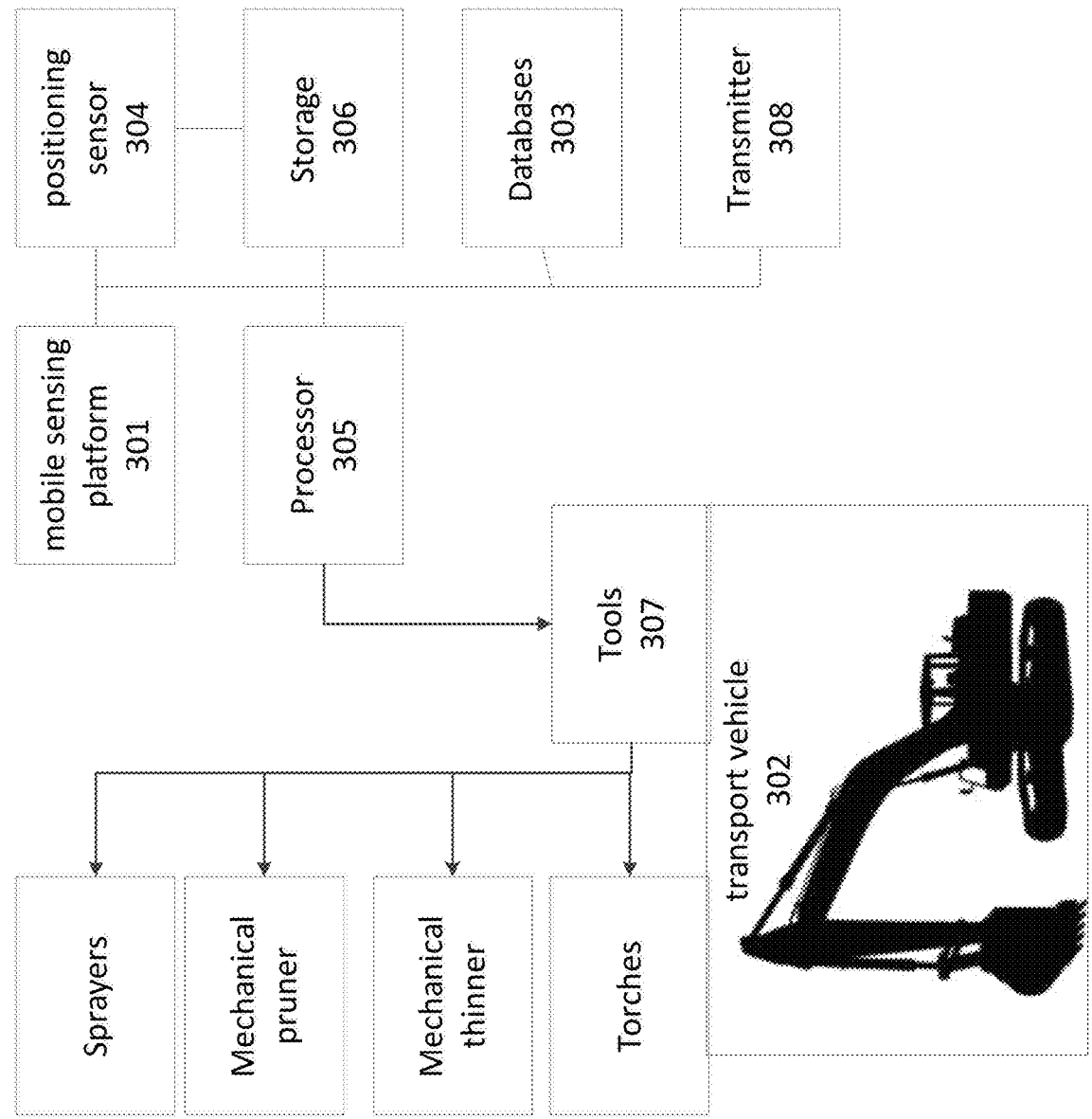
Figure 3B
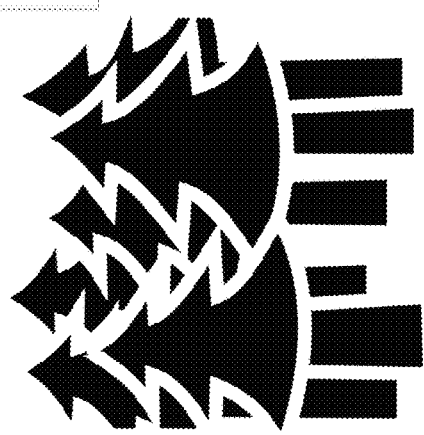

FORESTRY MANAGEMENT TOOL FOR ASSESSING RISK OF CATASTROPHIC TREE FAILURE DUE TO WEATHER EVENTS

CROSS-REFERENCE TO RELATED APPLICATIONS

The present application claims priority to, and is the National Stage of, International Application PCT/US18/27199 filed on Apr. 11, 2018, which claims priority to U.S. Provisional Patent Application No. 62/484,266 filed on Apr. 11, 2017. Each of the aforementioned applications is incorporated herein by reference in its entirety.

TECHNICAL FIELD

The present invention is related to systems and methods for accurately predicting catastrophic tree failure based on fused sensor data, and systems and methods for preventing and treating catastrophic tree failures using said predictions.

BACKGROUND

In recent years, forests have faced increasing threats from the effects of a changing climate, including more extreme temperatures, extended periods of drought which increase the likelihood and severity of forest fires, more intense flooding, stronger tropical storms, monsoons and hurricanes, and changes in atmospheric circulation and wind patterns. Along with the loss of protection for diverse plant species within the forest biome, increased risk of erosion with loss of topsoil, and loss of habitat for animal populations, these conditions lead to compromised stand integrity and an increase in the risk of tree loss through overthrow and stem breakage. The result of this is that the climate risk becomes greater over time, since tree loss from any source reduces the carbon sequestration capacity of a forest. Additionally, these tree failures pose a risk of economic loss to agricultural forests that harvest and process trees for timber or pulp, as damaged trees, which provide lower volumes of usable wood, are less valuable.

Recognizing the risk weather events play to agricultural forests, significant efforts have been aimed at predicting tree damage from severe weather. Mechanistic models for tree failure have been developed which model a tree as a cantilevered beam, as shown in FIG. 1, supporting loads from wind and gravity. FIG. 1 shows the effects of wind and gravity on a tree. The resistance provided by the root and soil system, as well as the mechanical properties of the wood, must exceed the forces of wind and gravity to prevent failure.

These separate, largely orthogonal, straight-line forces manifest as a rotational force due to the single moment connection of the tree with the ground. The stress that wind and gravity loads impart on a tree can cause failure through either physical breakage of the trunk, or "stem" ("stem breakage") or loss of anchorage through uprooting ("windthrow"). While these models offer relative simplicity for use, no prescription has been presented for how these models can be used to provide intelligent forestry management advice for large numbers of trees that vary in size, variety, and exposure, as happens in a forest setting.

Moreover, models do not currently make risk assessments of catastrophic failure at the forest population level. Modeling a large population of trees manually would be extremely labor intensive, making it impractical. Thus, where growers and foresters are interested in modeling a tree, they typically use reduced models that assume regularly shaped cross sections and tapers, rather than eccentric forms nature produces. These forms produce directional strengths and weaknesses in the trees based on the depth of the section along specific vectors, which can lead to strength profiles that vary from a normalized model, and that are better or less well equipped to respond to specific wind vectors. FIG. 2A shows the idealized form of a trunk currently used for the calculation of stem breakage. While taper can be applied over its length, changing the diameter along the length of the stem, it does not adequately represent the discontinuities of form a tree may exhibit in any particular segment, as depicted in FIG. 2B.

When predictions of catastrophic tree failure due to wind and gravity loads are made, they are typically calculated using gross approximations and reduced models, hampering the accuracy and real-world utility of the predictions.

Accordingly, a need exists for systems and methods that enable accurate prediction of catastrophic tree failure with high degrees of accuracy and precision, based on accurate measurements of each tree's structure.

SUMMARY OF THE INVENTION

In various embodiments, the invention provides systems, methods, and apparatuses for determining a risk of catastrophic failure for a tree based on a mechanistic model of physical characteristics of the tree. According to some embodiments, the systems, methods, and apparatuses can include a mobile sensing platform comprising one or more sensors for obtaining data, a transport vehicle configured to transport the mobile sensing platform, a positioning sensor configured to precisely calculate geographic coordinates of the positioning sensor and the location of the positioning sensor relative to a reference object as positioning data, and a processor configured to fuse the imaging data and the positioning data. With the imaging data and positioning data fused, conditions for catastrophic tree failure can be determined.

According to some embodiments, the one or more sensors can include a LiDAR sensor, an RGB sensor, a multispectral imaging sensor, a hyperspectral imaging sensor, a soil composition sensor, an ultrasonic sensor, and/or a sonar imaging sensor.

According to some embodiments, the positioning sensor achieves a centimeter level accuracy. In this way, the imaging data and the positioning data can be fused together at a highly granular level, thereby improving accuracy and precision of the measurements and predictions that are made thereon. In some embodiments, the positioning sensor includes an inertial measurement unit that calculates the change in location and orientation relative to the former position and orientation of the positioning sensor based on measurements of the sensor's inertia or magnetic fields. In some embodiments, the processor performs simultaneous localization and mapping using IMU and point cloud data to determine location and orientation in GPS denied environments.

The mobile sensing platform can generate an assembled point cloud and the processor can be configured to calculate dimensional and morphological data based on the assembled point cloud, and determine the conditions for catastrophic tree failure based on the dimensional and morphological data.

According to some embodiments, the systems, methods, and apparatuses can include a storage medium for storing the imaging data received by the mobile sensing platform and a transceiver for transmitting the imaging data. The processor can be configured to convert the imaging data received from the mobile sensing platform into a different format.

According to some embodiments, the systems, methods, and apparatuses can include a static database and a dynamic database. The static database can store associations between plant varieties and spectral signatures. The dynamic database can store forecasts of weather conditions in a particular locality.

According to some embodiments, the conditions for catastrophic tree failure are determined based on characteristics associated with the tree's species. The characteristics associated with the tree's species can include density, strength and/or allowable flexion. The tree's species can be determined by comparing multispectral and/or hyperspectral imagery of the tree with a library of spectral signatures.

According to some embodiments, the processor can also be configured to model the tree's stem horizontal profile at one or more heights above ground. The model includes anomalies from a circular profile and eccentricities of the tree stem structure. The processor can be further configured to fuse the model of the tree's stem horizontal profile with strength measures associated with the tree's species. The strength measures can comprise moisture content of wood, and damage to the tree stem. The model of the tree's stem diameter can be used to determine the conditions by which the tree's stem will withstand lateral, gravitational, and torsional loads without breaking.

According to some embodiments, the processor can be further configured to determine the form and size of the tree's root system and soil plate extents using species-specific heuristics of the morphological data. The processor can further be configured to determine the tree's counter moment potential based on an estimated soil plate weight calculated from the form and size of the tree's root system.

According to some embodiments, the mobile sensing platform generates an assembled point cloud. The processor can be further configured to determine a wind force applied to a tree using the assembled point cloud. The wind force can be based on a wind speed. The processor can be further configured to determine whether additional trees are surrounding and obstructing the tree based on the assembled point cloud data. The system, methods, and apparatuses can further comprise a weather database of wind projections. The processor can be further configured to create a tree profile based on the assembled point cloud. The tree profile can include cloud vertices associated with a canopy, stem and branches of the tree. The processor can be further configured to calculate forces applied at each location of the tree profile based on the wind projections, and based on contextual data related to the tree's environment. The contextual data can include the number and position of additional trees surrounding and/or obstructing the tree.

According to some embodiments, the processor can be configured to determine a wind speed and a wind pressure applied to the tree. The processor can adjust the wind pressure based on the degree to which the tree canopy is streamlined. The processor can be further configured to calculate bending and moment forces applied to the tree's stem, and strain experienced by the stem based on a bending modulus, density of the tree, volume of the tree, anticipated surface area capable of holding ice or snow, and projections for snow fall and ice accumulation.

According to some embodiments, the processor can be configured to calculate the tree's ability to resist bending, moment, and torsional forces applied to the tree's stem. The processor can also be configured to calculate a minimum wind speed that will cause the tree to fail. The failure can be stem breakage or overthrow According to some embodiments, the processor can be configured to calculate the tree's ability to resist bending and moment forces imparted by gravitational loads based on wind vectors and anticipated snow and ice accumulation predictions.

According to some embodiments, the processor can be configured to calculate the tree's ability to resist bending, moment and torsional forces applied to the tree's stem, and the tree's ability to resist moment imparted by gravitational loads, based on the external deformations of the tree's shape.

According to some embodiments, the processor can be configured to determine an expected failure force as a minimum force that will cause a failure in the tree due to forces applied to the tree's stem or forces imparted by gravitational loads. The processor can also determine a wind speed that results in the expected failure force.

According to some embodiments, the processor can be configured to generate a user interface that graphically displays a critical wind speed for a plurality of trees. The user interface can indicate which tree of the plurality of trees is most likely to fail.

According to some embodiments, the processor can be configured to determine a likelihood of the tree failing based on weather data that indicates a likelihood of wind speeds reaching the critical wind speed of the tree. According to some embodiments, the processor can be configured to determine an order by which a plurality of trees will fail based on their respective critical wind speeds. According to some embodiments, the processor can be configured to recursively simulate the failure of a tree from the plurality of trees based on the order, and recursively update the critical wind speeds of the remaining trees from the plurality of trees.

According to some embodiments, the processor can be configured to determine an ideal time and a set of specific trees that, when harvested or culled, provide maximum economic value of a stand. The maximum economic value of the stand can be determined by reducing the risk chances of catastrophic loss.

According to some embodiments, the processor can be configured to calculate a change in critical wind speed of the tree based on harvesting activities or a catastrophic loss affecting the tree or surrounding trees.

According to some embodiments, the processor can be configured to determine routing harvest transport based on the data retrieved by the positioning sensor, and based on avoiding obstacles and causing damage to the tree.

According to some embodiments, the processor can be configured to determine a disease vector moving through a forest based on spectral data obtained from the mobile sensing platform.

According to some embodiments, the processor can be configured to estimate the tree's harvest yield based on the morphological data of the tree, the tree harvest comprising board feet of lumber, volume of pulp, or biomass of waste.

According to some embodiments, the system estimates growth rates for trees based on their variety, and presents a crop recommendation. The crop recommendation can include a planting design that maximizes future harvests. It can also include a culling plan to maintain stand integrity.

According to some embodiments, the transport vehicle is a terrestrial or aerial vehicle. According to some embodiments, the aerial vehicle can include a fixed or rotary wing.

According to some embodiments, the transport vehicle is manually or autonomously navigated.

BRIEF DESCRIPTION OF THE DRAWINGS

To facilitate further description of the embodiments, the following drawings are provided in which:

FIGS. 3A and 3B show exemplary systems and apparatuses for determining a risk of catastrophic failure of one or more trees according to some embodiments;

Figure 1:
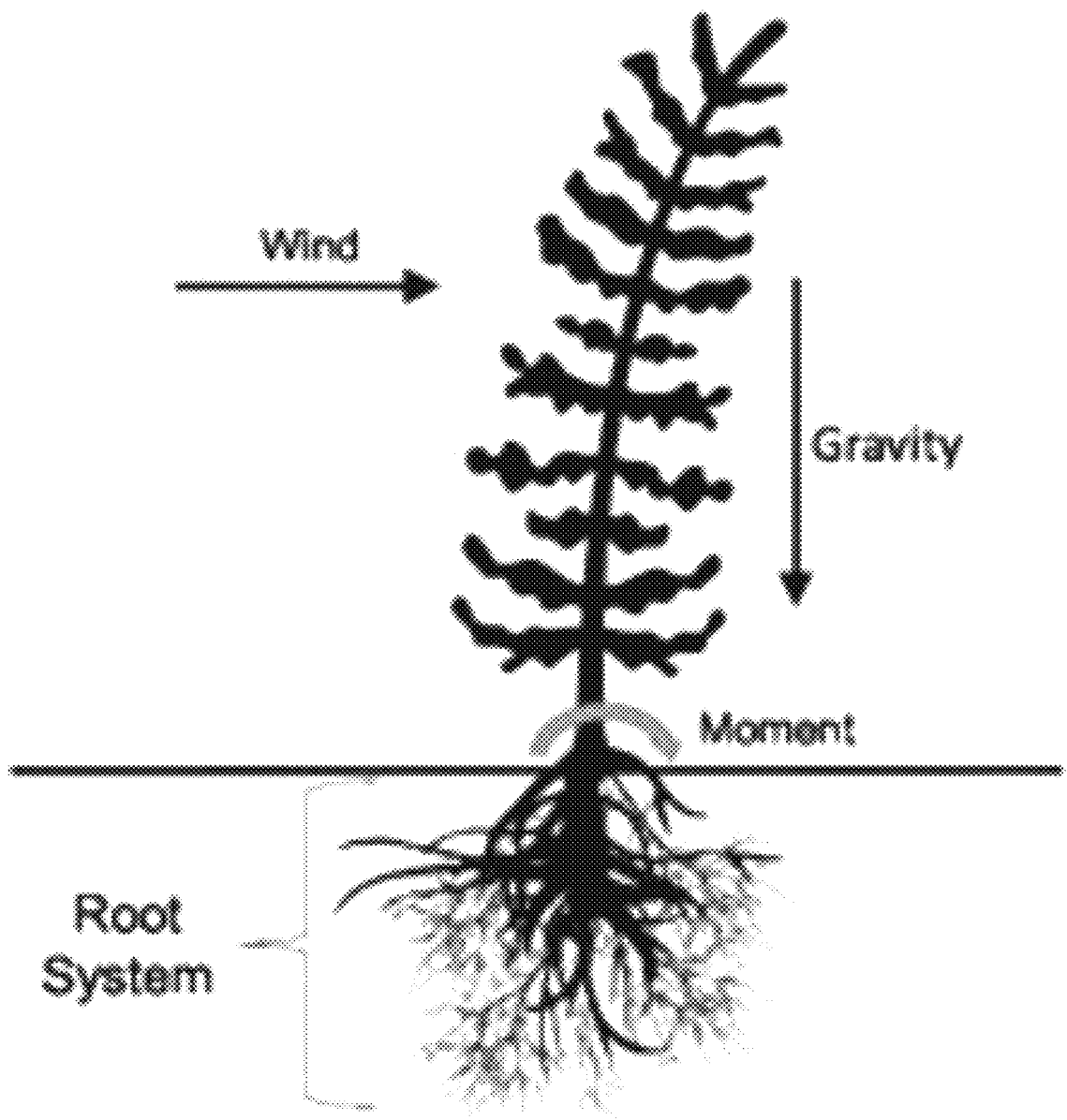
FIG. 1 illustrates mechanistic models for tree failure which model a tree as a cantilevered beam.
Figure 2B:
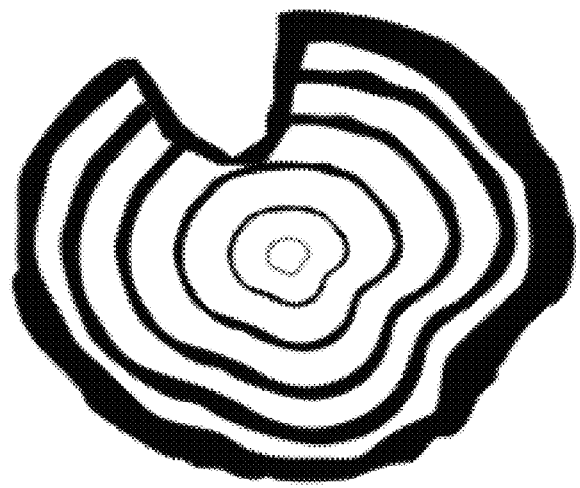
FIGS. 2A and 2B show the forms of a trunk for the calculation of stem breakage.
Figure 2A:
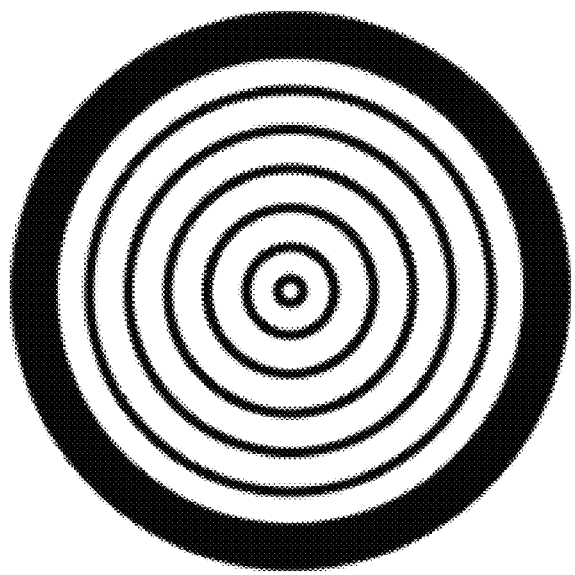

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

DETAILED DESCRIPTION

Systems and methods for calculating and modeling the risk of catastrophic failure are hereby disclosed. The systems and methods disclosed herein enable calculations and models to be applied to trees in stands and forests using a precise level of measurement detail, in conjunction with an advanced forestry information management system that allows users to include a wider array of precise inputs into the structural models of their holdings. The models can be based on mechanistic models of the physical characteristics of each tree, and enable the simulation of wind and gravity loads during extreme weather events for plants in a wooded area. The calculations and models can then be used to generate crop recommendations, which can be used by transport vehicles to implement treatment or development procedures such as culling, spraying, thinning, pruning, torching, or clearing.

Figure 3A:
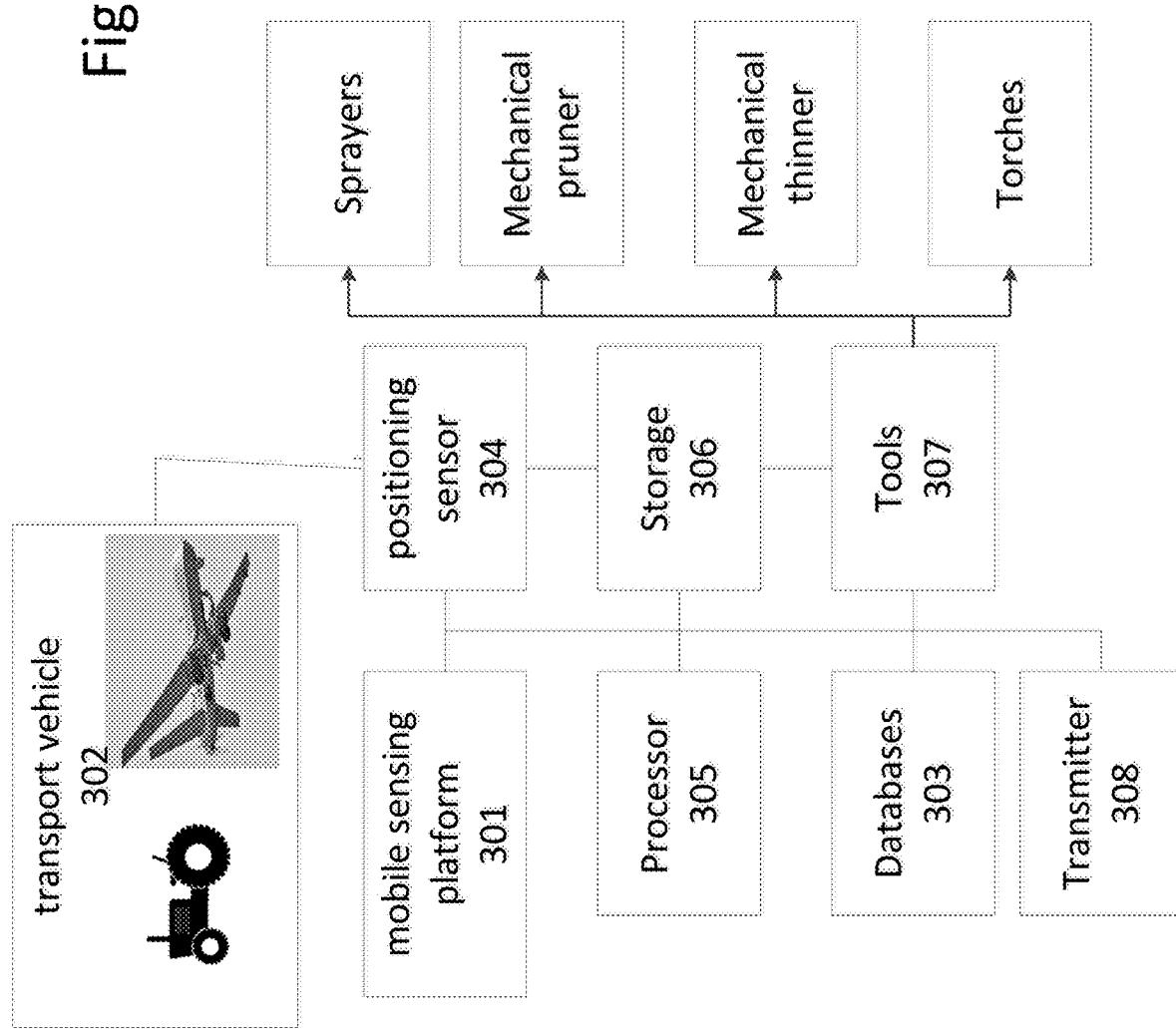

FIG. 3A shows exemplary systems and apparatuses for determining a risk of catastrophic failure of one or more trees according to some embodiments. In some embodiments of the invention, a system for determining a risk of catastrophic failure of one or more trees includes a mobile sensing platform 301 comprising one or more sensors for obtaining imaging data. The mobile sensing platform can be a high precision remote scanning platform used to obtain data at a high level of granularity. High-precision remote sensing technologies can include high resolution data attainable from sensors such as LiDAR and hyperspectral imaging systems. The sensors of the mobile sensing platform may include a LiDAR sensor, a multispectral imaging sensor, a hyperspectral imaging sensor, an RGB imaging sensor, a sonar sensor, a soil composition sensor, or similar sensors for collecting imaging data and determining the properties of a tree and its environment.

According to some embodiments, the system can include a transport vehicle 302 configured to transport the mobile sensing platform. In some embodiments, the transport vehicle can be a terrestrial vehicle or aerial vehicle that can be manually or autonomously navigated. The aerial vehicle can have a fixed or rotary wing. The mobile sensing platform can be mounted to the transport vehicle, and as the transport vehicle transports the mobile sensing platform through or over a forest or area of trees, the mobile sensing platform can be configured to collect, measure, and record point cloud data, spectral data, dimensional data, assembled morphological data, positional data, and orientation data with at least centimeter-level accuracy.

According to some embodiments, the systems, methods, and apparatuses can include one or more databases 303, a positioning sensor 304, a processor 305, a storage 306, one or more tools 307, and a transmitter 308.

The databases 303 can be static databases and/or dynamic databases. The static database can store associations between plant varieties and spectral signatures. The dynamic database can store forecasts of weather conditions in a particular locality.

The positioning sensor 304 can precisely calculate the geographic coordinates of the positioning sensor and the location of the positioning sensor relative to a reference object as positioning data as described more fully below. The positioning sensor can be, for example, a GPS, inertial measurement unit (IMU), or some combination of thereof. According to some embodiments, the positioning sensor is capable of achieving a centimeter level accuracy. In this way, the imaging data and the positioning data can be fused together at a highly granular level, thereby improving accuracy. For example, in some embodiments, the positioning sensor includes an IMU that calculates the change in location and orientation relative to the former position and orientation of the positioning sensor based on measurements of the sensor's inertia or magnetic fields. As another example, in some embodiments, the processor in conjunction with the positioning sensor performs simultaneous localization and mapping using IMU and point cloud data to determine location and orientation in GPS denied environments.

The processor 305 can be configured to fuse the imaging data and the positioning data. With the imaging data and positioning data fused, conditions for catastrophic tree failure can be determined. In some embodiments, the mobile sensing platform can generate an assembled point cloud and the processor can be configured to calculate dimensional and morphological data based on the assembled point cloud. The processor can then determine one or more conditions for catastrophic tree failure based on the dimensional and morphological data based on the assembled point cloud.

In some embodiments, the processor can be configured to convert the imaging data received from the mobile sensing platform from one format into a different format. For example, the processor can convert the imaging data from raw data formatted in rows and columns, into a delimited format, XML document, or similar data structure or file. The reformatted imaging data can then be more readily stored, accessed, and searched in a database or storage for subsequent analyses, measurements, or calculations.

The storage 306 can be used to store libraries or external data sources that are used as inputs for measuring and/or calculating tree parameters and physical properties as discussed in more detail below. In some embodiments, the storage can also be a storage medium for storing the imaging data received by the mobile sensing platform.

A transceiver 308 can transmit imaging data from the mobile sensing platform, positioning data from the position sensor, and other data stored or collected by the transport vehicle to and from other components of the system depicted in FIG. 3A and 3B such as the processor, storage, databases and tools.

Tools 307 are one or more devices, extensions, and/or adapters that can be coupled to or mounted onto a transport vehicle and carry out some action or treatment that is determined based on a measurement, estimation, or analysis of a tree as described herein. For example, a tool can be one or more dynamic rate sprayers configured to dynamically apply a spray (e.g., fertilizer or pesticide) to a tree. It may be determined, for example, that a tree or set of trees needs to grow taller or wider to change or modify the wind patterns of nearby trees to reduce the likelihood of tree overthrow or breakage; to address this need, the dynamic rate sprayers can dynamically target the tree or set of trees with fertilizer. As another example, the tools can include mechanical pruners, mechanical thinners (e.g., fellers, bunchers, clearcutters, and similar tools), or torches (for controlled burns) configured to dynamically remove, destroy and/or shape one or more trees. It may be determined that the overall wind pattern of one area of a forest would be better served by removing one or more trees; to address this need, the mechanical pruners, thinners, or torches can be used to remove such trees. FIG. 3B shows exemplary systems and apparatuses where the transport vehicle 302 implements treatment or development procedures such as culling, spraying, thinning, pruning, torching, or clearing, using the tools according to some embodiments.

In some embodiments, a LiDAR system is employed to calculate the distance from the mobile sensing platform sensors to objects in its environment. To accomplish this, a laser pulse is emitted in a known direction which is reflected back to the sensor when its path intersects with an object. The distance to the object is determined by measuring the round-trip time-of-flight of a light pulse emitted from a laser to a target and then back to a detector. The round-trip time-of-flight that is measured can be used to determine a precise measurement of the object's position in space relative to the position of the mobile sensing platform sensors. By passing the laser output through a rotating prism or mirror, a single light source can probe a 360° circle. When the LiDAR unit is placed on a mobile sensing platform, successive layers of distance measurements can be stitched together into a single three-dimensional model of a space. By using a global positioning systems (GPS) and an onboard inertial measurement unit (IMU), relative point positions can be resolved to a global grid, creating a precisely geo-located surface model of objects within range of the mobile sensing platform. Collectively, the measurements based on the LiDAR unit are called an assembled point-cloud. In some embodiments, the system performs simultaneous localization and mapping using IMU and point cloud data to determine location and orientation in GPS-denied environments, where a GPS is not accessible. Models of trees based on point clouds can achieve centimeter level accuracy. As described below, point cloud data and the models thereon allow for more granular inputs while increasing the overall area of analysis to the scale of an entire forest.

Point cloud data enables the precise modeling of true features of each tree in an area. The imaging data collected by the remote sensing platform can be used for structural analysis of the failure risk of each tree in a stand, forest or grove/orchard by calculating dimensional and morphological data based on assembled point clouds. For example, models based on three-dimensional LiDAR point cloud data enable the systems and methods to analyze the actual, eccentric shape of trunk sections and canopies, rather than assuming a smoothly-tapered cylinder for a trunk and hemispherical or conic canopy. As another example, assembled point clouds also reveal externally visible damage such as splitting, rot, or gouges. In this way, the systems, apparatuses, and methods herein provide a more accurate representation of each tree's structural resistance to moment forces throughout its stem's length, and reports features related to its valuation, including the volume of salable wood, pulp, or biomass each tree represents, or the tradable carbon sequestration potential of each tree.

The mobile sensing platform can be configured to collect raw phenotypical data. Phenotypical data includes any measurable data resulting from the expression of genetic characteristics relative to a particular environment, and includes morphological data, such as height, stem diameter, and canopy density; factors such as chemical characteristics, which can be determined from spectral measurement; and unique physical features such as patterns of growth, or the presence of infection. The raw phenotypical data can be batch processed into structural models of a tree. The structural models can include one or more descriptions of each tree's resistance to bending-and rupture-inducing forces, as well as how the entire structure of the tree becomes loaded by lateral, vertical, and moment forces from wind and gravity. In this way, the systems and methods herein can determine the risk of, and the conditions that lead to, catastrophic tree failure based on dimensional and morphological data measured and determined using the mobile sensing platform.

As explained above, the mobile sensing platform can be a high precision remote scanning platform used to obtain data at a high level of granularity. The improved level of granularity allows for increased accuracy both in relation to individual trees, as well as cumulatively, over a tree population. Embodiments of the invention thus provide the ability to cost-effectively measure individual tree metrics on the scale of entire forests, groves or orchards with centimeter-level accuracy. In turn, the accuracy of tree failure prediction is greatly improved.

Using spectral and/or other sensory data and/or data from external sources, the systems, apparatuses and methods can collect, create, and/or analyze soil characteristics that are relevant to assessing the resistance to moment provided by the weight of a soil plate. This can be, for example, the clay content of the soil. Such soil characteristics can help determine the degree to which the soil coheres to form a single mass and adheres to the roots of a tree. This in turn can be used to predict how a tree would resist moment forces. Other soil characteristics that can be used to determine a tree's ability to resist moment forces include the tree variety's characteristic root morphology, spectral characteristics, data from 3rd party sources such as the USDA NRCS maps, or any combination thereof.

In some embodiments of the invention, precise models based in part on mechanistic models can be used. For example, the precise models can be based on mechanistic models described in H. Peltola et al., *A mechanistic model for assessing the risk of wind and snow damage to single trees and stands of Scots pine, Norway spruce, and birch*, 29 Canadian Journal of Forest Research, 647-661 (1999); H. Peltola et al., *Model computations on wind flow and turning moment by wind for Scots pines along the margins of clear-cut areas*, 83 Forest Ecology and Management, 203-215 (1996); and H. Peltola et al., *Mechanical stability of Scots pine, Norway spruce and birch: an analysis of tree-pulling experiments in Finland*, 135 Forest Ecology and Management 143-153 (2000), all of which are herein incorporated by reference in their entirety. According to some embodiments, the effects of wind on a tree can be determined by:

$$F_1(z) = (\tfrac{1}{2}) c_d \rho u(z)^2 A(z) \quad (1)$$

where $F_1(z)$, $A(z)$, and $u(z)$ are the force, wind speed and cross-sectional area (respectively) on the tree at height z. The parameter $c_d$ is a dimensionless drag coefficient and p is the density of the air.

These mechanistic models use tree stems and/or tree trunks as natural embodiments of cantilevered beams, which, in architecture, are beams supported at a single end by a moment connection. Such models ground the calculations for estimating how wind and gravity loads affect the members of the tree using structural engineering principles.

Several aspects of a failure can be predicted. For example, the critical wind speed that causes structural failure can be predicted. Similarly, the mode of failure of a tree can be predicted, which may be for example, by stem (e.g., trunk) breakage or by overthrow (e.g., uprooting). Critical wind speeds can be provided for a local population using an annotated mapping solution that describes both the precise location and orientation of each tree, the path of dominant wind patterns, and the critical wind speed leading to failure of each tree. The systems, apparatuses, and methods described herein can enable users to analyze the effect of gravity loads on trunks deformed (e.g., bent) by horizontal forces associated with average seasonal wind loads. These loads include the tree's own weight, as well as snow and ice loads.

In some embodiments, the systems, apparatuses, and methods herein consider the wind speeds necessary to overthrow or cause stem breakage to trees at the perimeter of stands and forests, where they are most exposed both to consistent and to extreme wind pressure. The systems and methods consider lateral forces due to wind pressure on the canopy and stem as well as vertical forces due to the weight of the tree, as well as wind and ice loads. These are used to calculate the total moment force acting on the tree. This force is then compared to the resistance to overthrow provided by the weight of the tree's soil plate. It is also compared to the modulus of rupture (MOR) of the tree's stem, which represents the force needed to break it.

To calculate the bending moment from wind pressure, a model can calculate the effect of wind on each part of the tree. Less precise systems, apparatuses and methods can model these forces using geometric approximations of the area on which pressure can be applied such as a sphere or cone for a canopy, or a regularly tapered column for a stem.

However, a simple geometric shape used to estimate the tree can be a significant source of error if (as is common in nature) the tree exhibits irregularities in shape. Using LiDAR, the systems, apparatuses, and methods herein can model the area of the canopy and trunk with centimeter level accuracy, incorporating eccentricities such as heterogeneous canopy density, and irregularly shaped canopies, stems, and branches. The use of LiDAR enables investigators to model the area of the canopy and trunk with significantly greater accuracy than a simple polygon assignment to A(z) could accomplish. For example, a three-dimensional measurement of a tree permits consideration of eccentric voids in tree canopies when calculating biomass, and allows a heterogeneous canopy density to be fully characterized, as demonstrated in FIGS. 4A-4C which shows how the cross-sectional area of the tree changes with height.

Figures 4A, 4B, 4C:
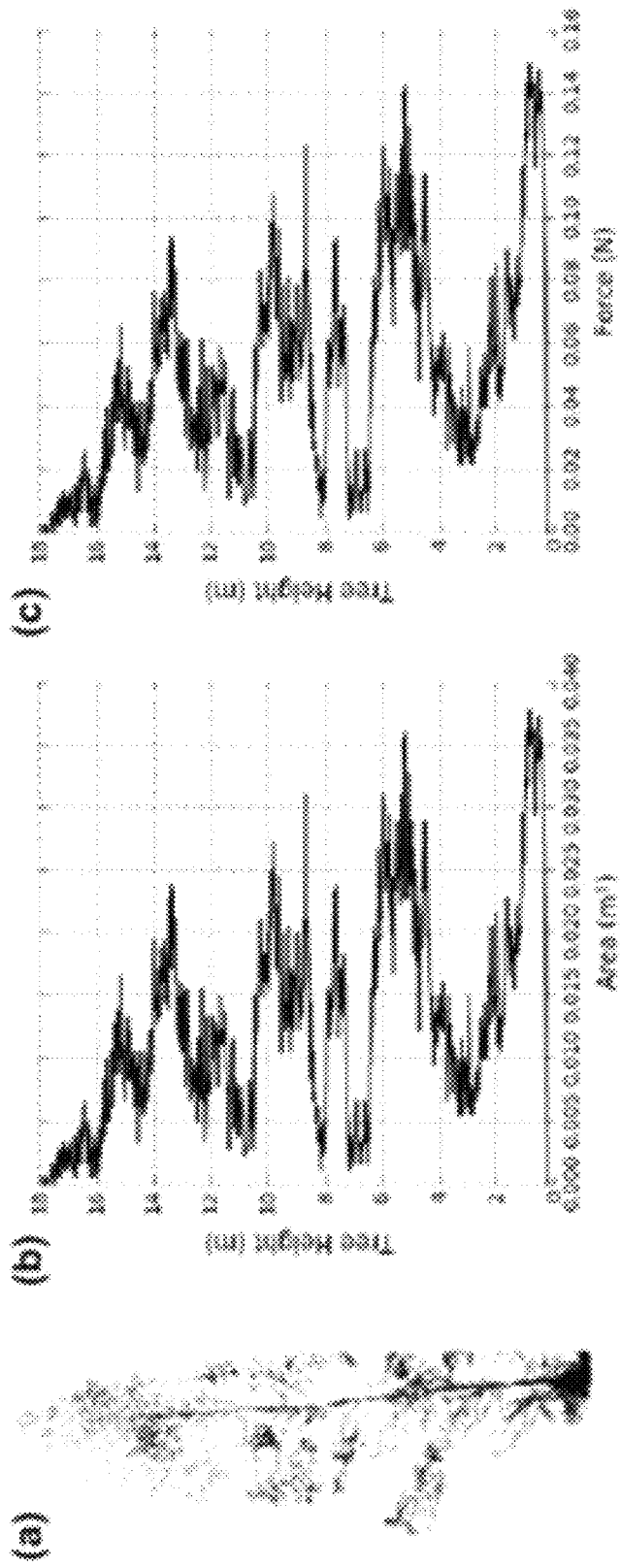
FIGS. 4A, 4B, and 4C show exemplary point cloud data measurements of a eucalyptus tree according to some embodiments.

FIGS. 4A-4C show exemplary point cloud data measurements of a eucalyptus tree according to embodiments of the invention. FIGS. 4A-4C show how LiDAR can observe the trees leaves, branches, and the trunk. FIG. 4B is an examination of how the cross-sectional area changes throughout the height of the tree as determined from the point cloud in FIG. 4A. FIG. 4C shows calculated force due to wind on the tree using Eq. (1), with a 10 m/s wind, a density of 1.275 kg/m$^3$, and a drag coefficient of 0.62. This information can be used to calculate wind force on the tree at any given height as demonstrated in FIG. 4C. As FIGS. 4A-4C show, the LiDAR data allows for an unprecedented level of detail to be extracted throughout the entire height of the tree enabling much more precise data to be used in models like Eq. (1).

Figure 5:
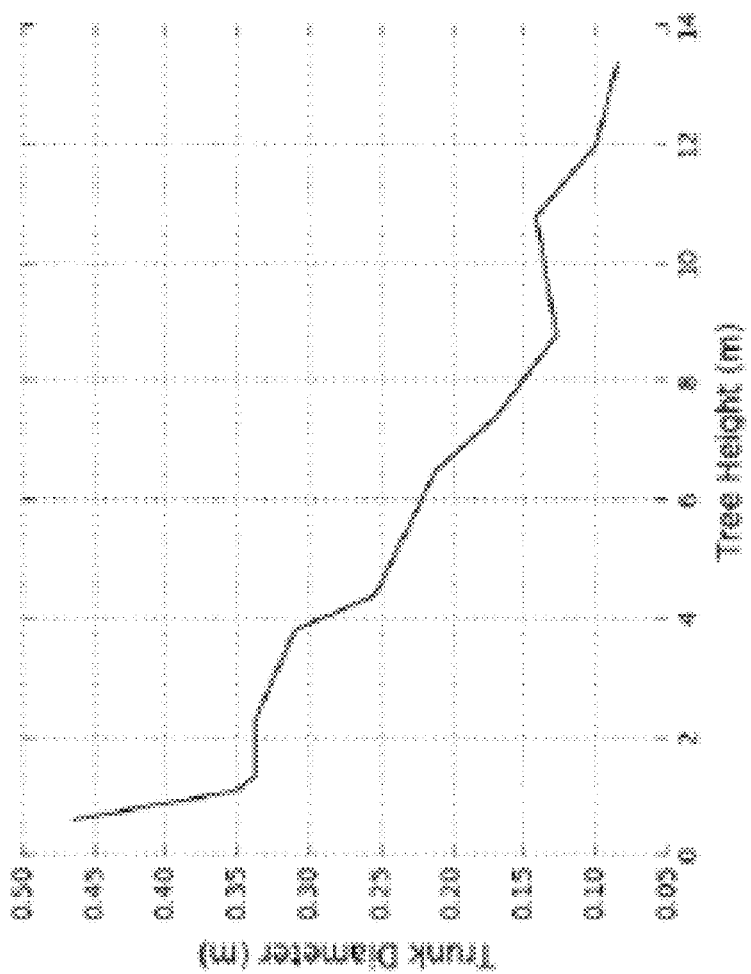
FIG. 5 shows exemplary measurements of trunk diameter as a function of tree height according to some embodiments.

The point cloud data can also be used to predict when the wood of the tree will fail due to wind-induced stress. Because the trunk of the tree is visible in the point cloud throughout much of the tree height, its diameter can be extracted as a function of height. FIG. 5 shows exemplary measurements of trunk diameter as a function of tree height according to embodiments of the invention. The trunk diameter can be extracted from the point cloud data in FIG. 4A. The point cloud can also enable the tree to be profiled at any point along its span. Such measurements can be used to calculate how many usable board feet of lumber can be harvested. They further allow stresses on the stem to be modeled that take into account the aerodynamic properties of the particular structural configuration.

By considering the wind forces from FIG. 4C the methods, apparatuses, and systems disclosed herein can provide an estimate of how a tree trunk will break, and what critical wind speed provides the necessary force to do so. In this way the LiDAR derived data allows for a more complete three-dimensional modeling of the tree, providing the measurements for calculating the forces that induce structural failure.

The wind force hitting the tree varies with both the landscape of the approach, as well as with the height above the ground. This profile can be estimated at height z with the formula:

$$u(z) = \frac{u}{k}\ln\left(\frac{z-d}{z_0}\right) \quad (2)$$

where u(z) is the mean wind speed, u is the aerodynamic characteristic of friction velocity, $z_o$ is the roughness length, d is the zero plane displacement, and k represents von Karman's constant. The base measurement for a canopy area can be assumed to be taken in a condition of still air.

Wind pressure, in addition to its effect on the bending moment in the trunk, causes the canopy to become more streamlined, thereby presenting less area to the wind force. The effect of streamlining increases with wind speed such that speeds less than 11 m/s yield ~, 20% area reduction, on average, whereas speeds greater than 20 m/s produce an area reduction of ~60%. Between 10 and 20 m/s the area reduction ($S_t$) is approximately defined as:

$$S_t = \frac{10}{u(z)} - 0.10 \quad (3)$$

for u in units of m/s.

Some embodiments of the invention compute bending and moment stresses on a tree as they accumulate. For example, stresses created by gravity loads can be combined with those resulting from horizontal wind loads to analyze the total stress affecting a tree. That is, once significant bending is introduced, vertical forces due to the inherent weight of the tree and external factors such as the weight of ice and snow can be considered. These forces act in the same direction as the wind, and can be calculated using the following:

$$F_2(z) = M(z)g \quad (4)$$

where $M_z$ is equal to the combined green mass of the stem and crown with the snow and ice loads as a function of height. The parameter g is the acceleration due to gravity at the surface of the Earth.

Figure 6B:
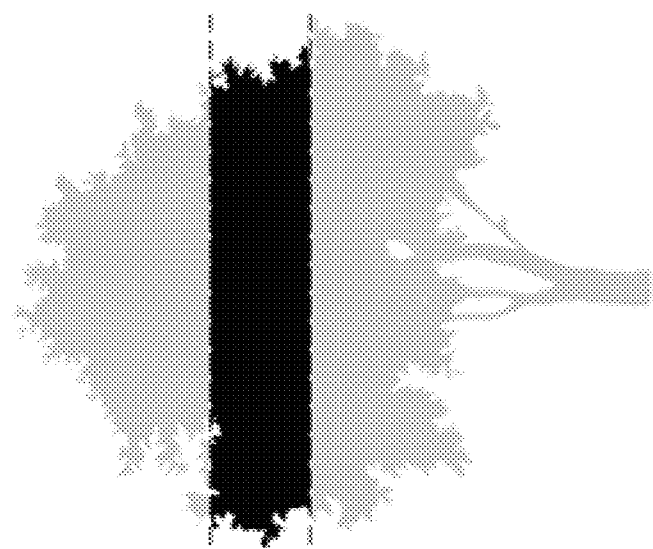
FIGS. 6A and 6B show segments of a tree for determining surface area to the wind on one side, resulting in torsion around the centroid of the stem.
Figure 6A:
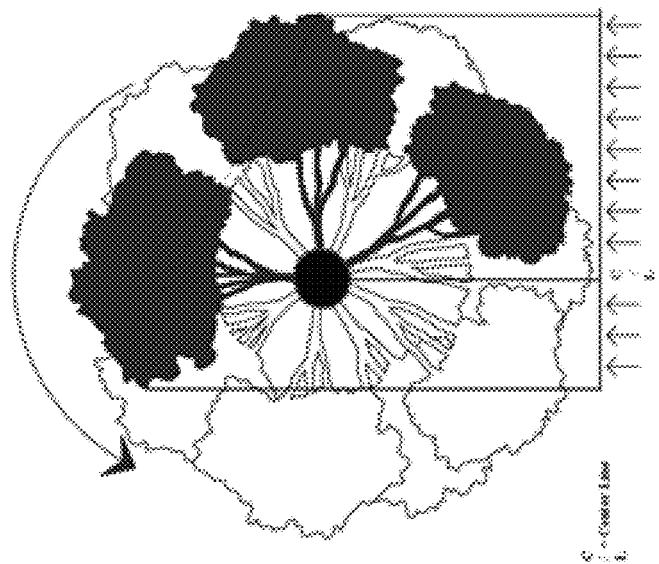

In segments of the tree, branches are distributed around the tree in such a way that bi-lateral symmetry relative to the direction of wind forces is unlikely. The tree presents a larger surface area to the wind on one side than it does on the other, resulting in torsion around the centroid of the stem, as shown in FIGS. 6A and 6B. This turning stress can be experienced in different directions over the length of the stem, loading additional stresses into the wood of each segment which can be considered in the calculation of bending and moment.

Because the structure and canopy of trees are not symmetrical, wind forces are distributed unequally to the sides of the trees along their height. As a result, the wind forces impart rotational forces along the axis of the tree's stem, which can vary in strength and direction at different heights above ground, depending on the distribution of limbs and leaves in the plane perpendicular to the vector of the wind. The varying impact of the wind on the different sides of the tree introduces torsional forces into the comprehensive model of stem and moment stresses. By measuring the precise structure of the canopy and its supporting structure, these forces can be included in the calculation of total stresses experienced by the tree, and provide a more precise model of the comprehensive effects of the wind at different speeds on the tree.

The green mass of the canopy can be calculated from the LiDAR point cloud model, while the value for the snow and ice load can be derived from the area of a horizontal projection of the unstreamlined crown on the ground surface, multiplied by the predicted snowfall, and distributed over the height of the crown.

These formulas can be used to calculate, at any point along a tree's height, including its root system, the turning moment imparted to the tree by the forces of wind and gravity. The addition to overall moment from an extreme wind loading due to wind gusting over any 1 m height segment can be modeled based on the height on the stem (z) adjusted for horizontal displacement.

The maximum force applied to a tree can be calculated based on a gust factor (e.g., a correction factor for wind gusts) and a gap factor (e.g., a constant accounting for wind shielding by other trees). These factors are dependent on the environmental features that can be determined from LiDAR models than show tree height, spacing, and distance from the edge of the stand. These calculations can been determined in wind tunnel experiments, and can be independent of tree variety.

By default, the gust factor can assume an infinite open area in the direction of the wind. The calculations can be adjusted based on whether other trees or features are in the wind path. The gap factor measures the size of the upwind gap in tree heights, with a gap greater than ten tree heights treated as being infinite.

Once these adjustments have been applied to each of the vertical segments of a tree, the total maximum turning moment at the base of the tree can be calculated as the sum of the turning moments for each section in a tree of height (h):

$$T_{max} = \Sigma_{z=0}^{h} T_{max}(z) \quad (5)$$

This turning moment can cause catastrophic failure to the tree in the following ways. If this force exceeds the root-soil plate weight, the tree will be overthrown, or uprooted. The rotational forces can cause the tree to fall, pulling the root-soil plate out of the ground. In this failure scenario, the total turning moment must exceed:

$$RS_{sup} = \frac{g \times RS_{mass} \times RS_{mean}}{A_{rsw}} \quad (5)$$

where $RS_{sup}$ is the supporting moment of the total root-soil plate anchorage, $RS_{mass}$ represents the mass of the root-soil plate, g is the gravitational constant and $RS_{mean}$ is the mean depth of the root-soil plate volume (cone) based on the width and depth of the root-soil plate. $A_{rsw}$ represents the root-soil weight as a proportion of the below-ground anchorage (dimensionless).

Another way the turning moment can cause catastrophic failure is if the turning moment exceeds the Modulus of Rupture (MOR), which is the maximum allowable tension stress for the outer fibers of the tree stem. If this happens, the stem will break. This is calculated from the breast-height diameter (DBH) of the tree and the MOR of the green wood of the particular variety using the formula:

$$STEM_{res} = \frac{\pi}{32} \times MOR \times DBH^3 \quad (6)$$

A tree will break if the total maximum turning moment at a particular elevation exceeds this resistance to that type of moment at that same height. The mode of failure is determined by the failure scenario reached as a result of the lower wind speed, based on the total moment calculation listed above. Wind profiles from weather agencies provide average and maximum wind values from which the likelihood of local conditions exceeding the minimum failure point of a tree can be determined.

Constants related to the strength, flexibility, and weight of specific tree varieties and soil conditions, can be predetermined. Risk predictions can then be batch processed from databases containing the data sets collected by the mobile sensor platform.

In some embodiments, data from multiple sensors of the mobile sensing platform can be fused to determine conditions for catastrophic tree failure. For example the imaging data and positioning data can be fused together using a combination of time stamps, and/or position stamps. In some embodiments, a pre-stored, previously generated, or previously simulated map of trees could be used to facilitate the fusion of sensor data. For example, a map of spectral signatures of each tree can be generated or simulated based on assumptions, estimations, or external data. The map can then be used to estimate when the mobile sensing platform would have expected to receive or detect a tree with the spectral or point cloud data of the tree. In some embodiments, the map could be a map of known locations of saplings or planted trees along a path or route. The path or route can then be loaded into a transport vehicle, and depending on the speed, acceleration, and distance traveled by the transport vehicle, the mobile sensing platform can determine which of the known saplings or planted trees it is collecting data on. In turn, with the specific sapling or planted tree that is associated with a particular set of collected data, the collected data can then be fused together. The fused data can then used to determine the conditions for catastrophic failure.

In some embodiments, the mobile sensing platform may detect the absence of a tree at a certain location where it would have expected one to be standing based on the preloaded route or path. The tree may be absent because for example, it was uprooted or damaged by a catastrophic event. To confirm that the tree is absent due to some catastrophic event, as opposed to some other error in mobile sensing platform or transport vehicle, the mobile sensing platform can analyze the profiles of nearby trees and confirm that those profiles and locations match what it was expected to detect.

According to some embodiments, fusion of the data from multiple sensors can occur on the mobile sensing platform and in real time as the transport vehicle travels over and/or through the forest. The fusion of the data from multiple sensors can also occur in a remote database, server, and/or computer, in real-time, or after the transport vehicle has travelled over or through a forest collecting data with the mobile sensing platform.

In some embodiments, hyperspectral imaging data can be combined with three-dimensional point cloud data, and mechanistic models of catastrophic failure for efficiently calculating the risk of structural failure of trees from wind and gravity loads for every tree in a specific forest environment. Hyperspectral imaging can provide a tree's variety, which relates to the inherent strength of the wood, the tree's health status, which relates to structural integrity, and root system profile, which relates to its moment resistance.

In some embodiments, data from multiple sensors can be fused to allow variety-specific traits, such as the density and flexibility of the wood, to be assigned to each tree. In some embodiments, the data can be processed in connection with a library of tree characteristics. For example, the model can determine tree variety based on spectral characteristics of the tree. This can be done by, for example, accessing a library of tree varieties and their respective spectral characteristics, and finding a tree variety with a matching set of spectral characteristics to those recorded for a particular tree. The model can then retrieve certain traits associated with the variety from the library. By fusing data sets from different sources, the systems and methods of the invention can efficiently calculate how stems are affected by wind, how they support weight from snow and ice, and how those forces interact with each other along the tree structure as the tree deforms in response to the total forces acting on it at a given point in time. In some embodiments, the systems can be used to specify the requirements for engineered solutions for reinforcing specific trees in anticipation of force loads in excess of their tolerances.

The point clouds generated by the LiDAR measurements enable the systems and methods disclosed herein to account for eccentricities of the unique structural system of each tree. For example, the systems and methods disclosed herein can account for eccentricities in the tree trunk over its height, rather than assuming a smooth taper, and the asymmetries in canopies. In turn, this enables users to predict how such eccentricities might affect the structural integrity of each tree individually and collectively under a range of environmental circumstances.

Since cross sectional area is one of the features used to determine MOR, being able to account for the stem section, including damage that may not have felled the tree, will allow increased precision in moment and stress calculations.

The systems and methods disclosed herein can be used for a variety of managerial functions because they provide a better understanding of how trees may fail. For example, they can provide decision support for culling and harvesting by giving a basis for determining the value of a particular tree, since both the quantity and quality of wood can be compromised in the event of catastrophic failure, and the expense of removal can increase if a tree is not cleanly harvested.

According to some embodiments, the systems, apparatuses, and methods also calculate the likelihood of catastrophic failure for use with financial models of the costs associated with extreme weather events. These models can include the risk of further tree loss due to changes in a stand's wind profile from the loss of wind protection, the loss of topsoil due to increased erosion where tree root systems are disrupted, or the loss of carbon sequestration capacity, including the value of any attendant financial benefits, from losing tree canopies.

Understanding how a tree is likely to fail and what other objects are located in its immediate vicinity further helps growers determine the potential for damage and financial loss that catastrophic tree failure would represent, whether and how to try to reinforce trees at risk of wind and gravity load damage, and whether there is a practical way to protect neighboring objects from the corpus of a falling tree. Thus, some embodiments of the invention enable users to analyze and predict the physical and financial losses associated with weather-induced catastrophic tree failure based on specific predicted conditions, such as wind speed and snow fall.

Some models can be used to predict the volume of marketable timber, wood pulp, and biomass present in a tree, stand, or forest. It can also be used to predict the carbon sequestration capacity of each tree. This data is valuable to sellers of forest products, producers who use those products as raw materials, as well as economists, financiers, and others involved in the various markets for forest-grown commodities, including carbon credits.

In some embodiments, the systems, apparatuses and methods enable users to perform catastrophe calculations over a number of the trees spread over a given area and manage interaction effects between the trees in a stand. Specifically, some embodiments of the invention enable foresters to consider the role of particular trees within a stand, and to evaluate various planting and harvesting schedules and plans.

Further embodiments provide the ability to analyze the risk of cascading failure within a wooded area, based on understanding how the failure of one tree affects the levels of force experienced by other trees in the area, thereby, changing the likelihood of their failure.

The modeling of complex interrelationships among elements in an ecosystem can be configured to be updated or modified based on changes to one or more input parameters. For example, such complex interrelationships can be recalculated to account for real or forecasted changes in model parameters, such as for example, the loss of particular trees. The models can thus iteratively and/or recursively calculate and map the failure probability of a tree in a stand or forest.

By providing the ability to run multiple scenarios that model the presence or loss of trees with particular characteristics at specific locations, the systems, apparatuses, and methods allow growers to evaluate the effect of different harvest strategies on the health of a stand. In this way, growers can avoid inadvertently weakening a stand through actions such as reducing a wind break provided by perimeter trees, or selectively removing a tree that is integral to a network of interwoven roots. It is also possible to project the economic and environmental value of the trees in a forest in order to manage the timing of harvest for individual trees in future periods, or project the effect of clear cutting a particular range of trees on surrounding stands.

In some embodiments of the invention, the systems and methods provide a forestry management decision support tool for an entire forest at the granularity of individual trees. It can thus facilitate decision making confidence regarding procedures, such as for example, choosing which trees are safest to harvest or cull at a particular time, or where, when, and what varieties to plant to decrease the failure risk of other trees in a stand, grove or forest in the future.

Some embodiments of the invention enable foresters and growers to understand the value of a specific tree by considering its role from the perspective of the surrounding ecosystem. By modeling how the loss of a particular tree will affect the wind forces experienced by its neighbors, the system is able to provide a basis for comparing the relative value of a particular tree if it were to be left in the ground where it could continue to protect other assets, compared to its post-harvest values. This provides an important tool for decision support among foresters and growers during processes such as culling, harvesting, planting, and other operations.

It can be used to assist how growers plan their planting, harvesting or culling activities based on a stand's structural needs and capacity. For example, trees with suitable characteristics to provide wind protection to other trees can be intentionally planted on the windward side of a stand. Conversely, those trees providing wind protection can be spared during harvest.

Some embodiments of the invention further enable batch processing of raw sensor data. Batch processing creates comprehensive and consistent modeling of trees in a population faster than individually modeling those trees. Further, it limits the introduction of errors associated with manual data entry.

The systems and methods disclosed herein can be used to forecast the loss of secondary trees due to the effects of wind and gravity by taking into account planned harvests, modeled disease vectors, weather events, or other man-made and natural causes that may change the number and characteristics of trees in an area. This analysis can also be used to predict the loss of carbon sequestration capacity associated with the canopies of trees that may be lost in an event.

Models of forested regions showing ground elevations, obstacles, and the spatial relationships of trees allow growers to plan routes for harvest vehicles that consider environmental damage to the forest, and minimize resource expenditures. According to certain embodiments, the invention also records the relationship of underbrush to trees and their branches, which can be used to plan interventions to reduce the risk of wildfire, as well as to calculate the amount of harvestable biomass available for use in fuel production. In some embodiments, the terrain, trees, and other objects in a forest or grove can be mapped to allow foresters and growers to calculate vehicle paths to specific trees for harvest or cleanup that permit safe passage and that cause the least damage to the local environment.

In some embodiments, the systems and methods disclosed herein can be used to analyze how climate change affects such factors as the severity of wind events and snow fall, resulting in the loss of trees that may have survived in milder conditions. For example, federal and state agencies can use the systems and methods disclosed herein to investigate the effect of climate change and how the loss of specific trees will affect such concerns as the spread of forest fires, flooding, mudslides and other occurrences related to fallen or lost trees.

These models will facilitate the process of revaluing large areas of woodland or permanent crops, the products they generate, and the markets they serve in the wake of major weather events, offering insight to watchers of tree-based markets and commodities.

In addition to providing valuation information of the land, according to some embodiments of the invention, the systems and methods disclosed herein can provide insurers with relevant additional information regarding their risk assessment and valuation of commercial properties used to grow trees for agriculture or recreational purposes.

Figure 7:
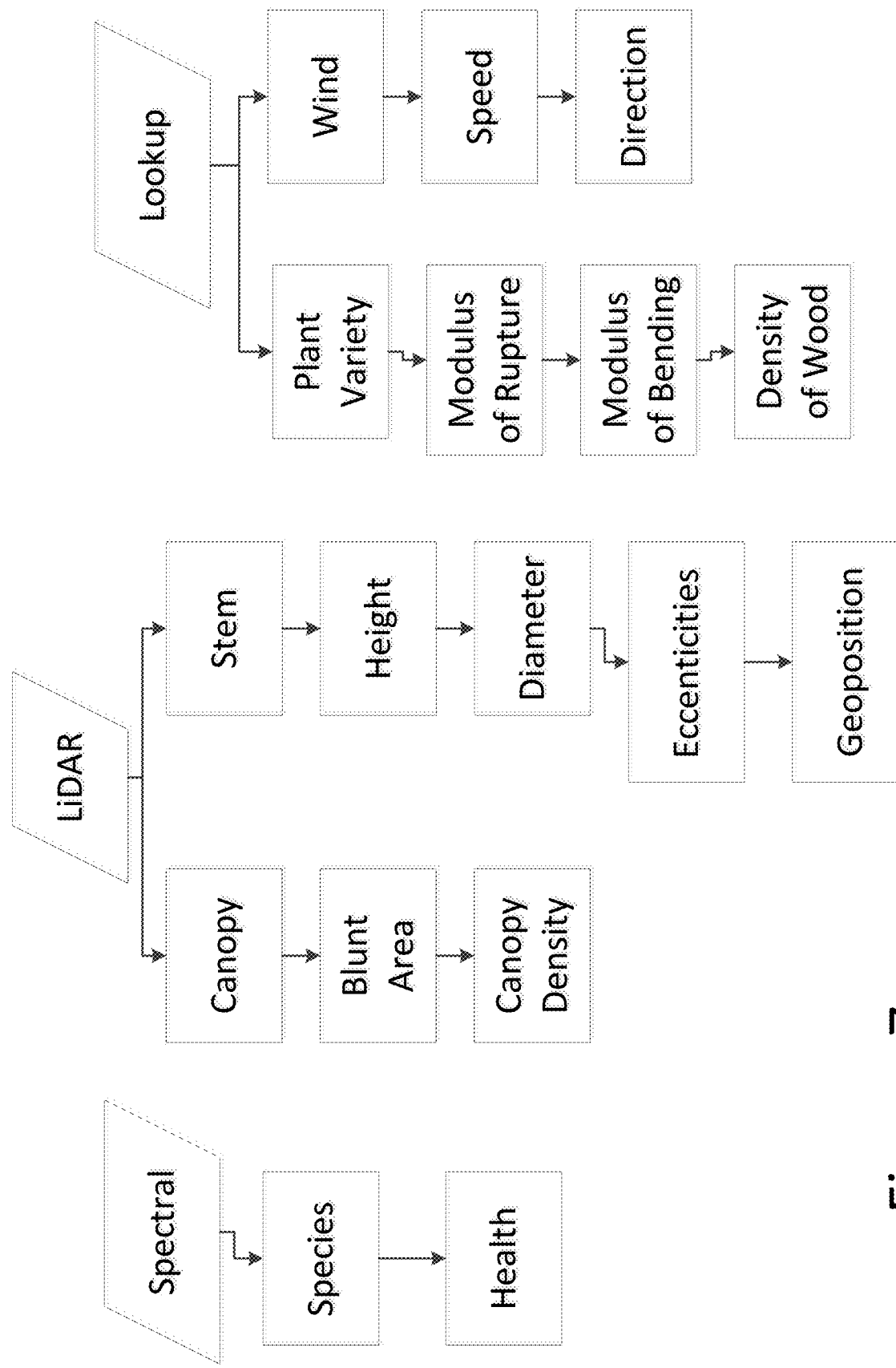
FIGS. 7, 8, and 9 show inputs, information sources, measured tree parameters and physical properties, and outputs that are generated by the systems, apparatuses, and methods according to embodiments of the invention.
Figure 8:
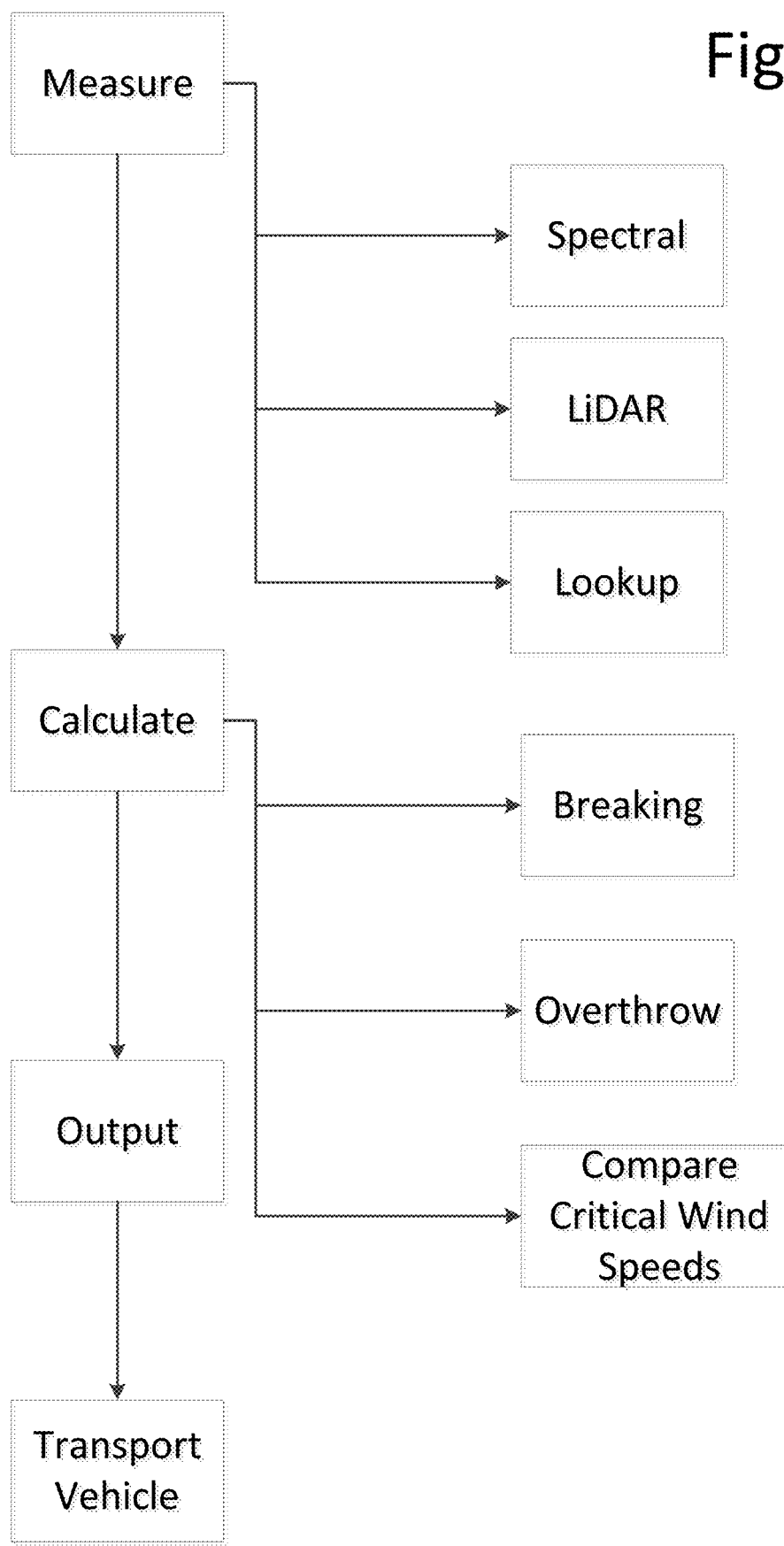
Figure 9:
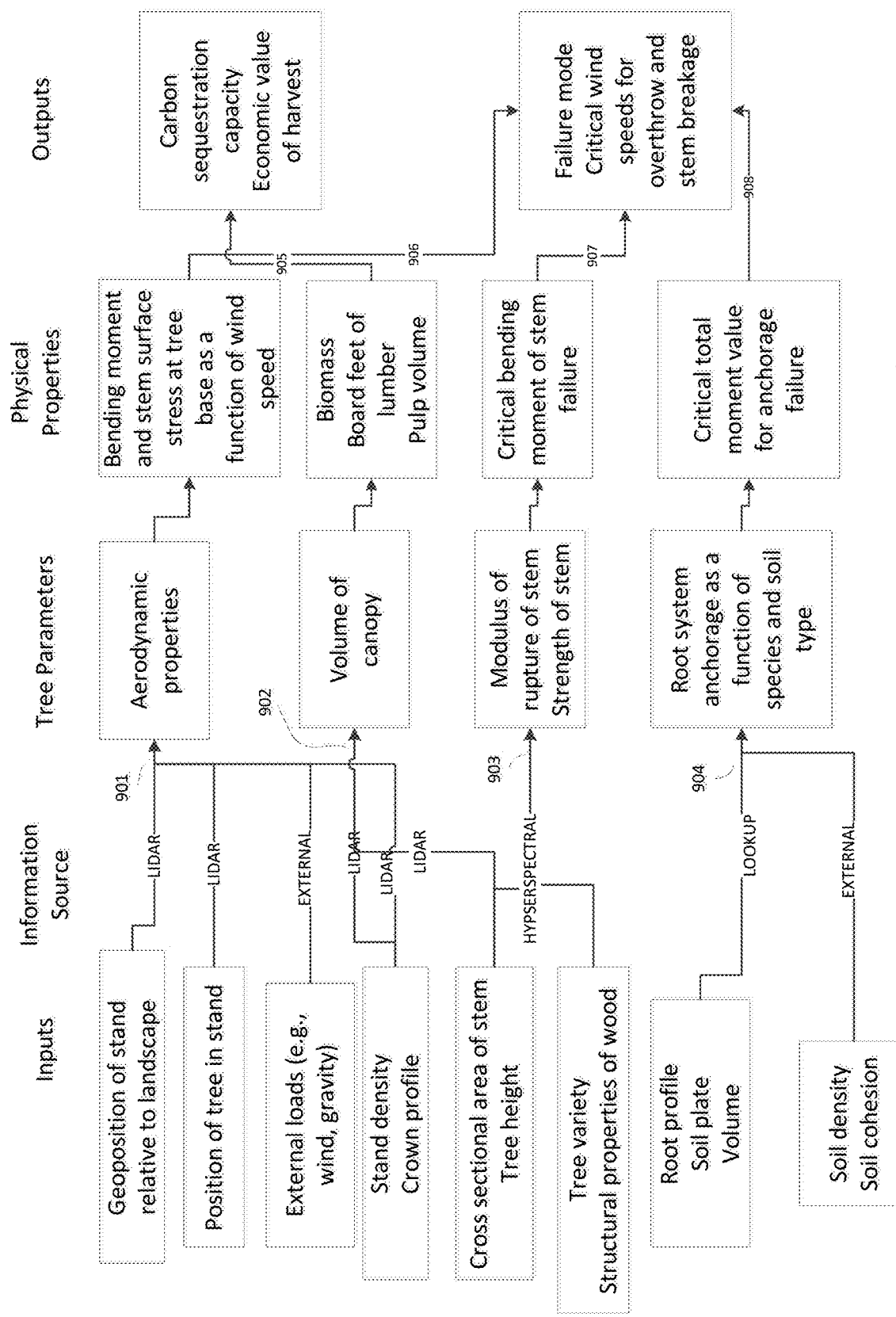

As described above, the systems, apparatuses and methods disclosed herein provide the ability to accurately model tree stem stress by incorporating direct LiDAR measurements of the trees. FIGS. 7-9 show inputs, information sources, measured tree parameters and physical properties, and outputs that are generated by the systems, apparatuses, and methods according to embodiments of the invention. Inputs can include tree species and tree health, which can be obtained from spectral sensors. LiDAR information sources can be used to obtain canopy and stem inputs. Canopy inputs can include blunt area at each segment, and/or density area at each segment. Stem inputs can include tree or stem height, diameter, eccentricities, and/or geoposition. Lookup inputs can include plant variety, modulus of rupture, modulus of bending, density of wood, and dominant wind information. Dominant wind information can further include speed and direction.

Tree parameters and/or physical properties can be calculated with the aforementioned inputs. For example, the critical wind speed at which a tree would break can be calculated by determining the environmental effect of the wind in a clear area. The stem profile in the direction of dominant winds can then be determined. This can include both the depth and strength of the dominant winds. The allowable stress from a tree segment shape and MOR for each segment can then be determined. A canopy profile in direction of dominant winds can then be calculated. The force(s) of wind acting on each foot of linear height for a specific wind speed can then be estimated. The force(s) of gravity acting on each foot of linear height based on bending due to wind speed can then be estimated. The stress in the stem at each segment of linear height based on the aforementioned forces and distance from segment (i.e., leverage) can then be determined. The calculated stress can then be compared to the calculated MOR for each segment. The wind speed for the above calculations and estimations is iteratively increased until the stress exceeds MOR in some segment. The value that exceeds the MOR is then recorded as the critical wind speed for breaking the tree.

As another example, the critical wind speed for causing overthrow can be determined by consulting a soil map such as the USDA NRCS soil maps, to determine bulk density and porosity of soil. A third party weather service can then be used to recall rain events, and calculate evapotranspiration from soil profile to determine bulk soil density. The weight of a soil plate, which provides resistance to moment forces, can then be estimated from bulk soil density and expected soil plate volume. This can be based on tree variety and morphology of visible features. The forces can be summed in the stem starting at a height of 0' at an average recorded wind speed for the area. The wind speed can be incremented until moment forces exceed resistance. The wind speed value at which the moment forces exceed resistance can be recorded as the critical wind speed for overthrowing a tree.

In some embodiments, the lower of the critical wind speed for overthrowing a tree and the critical wind speed for breaking the tree is the Overall Critical Wind Speed for the tree. Whichever mode of failure corresponds to the Overall Critical Wind Speed can be output as Anticipated Mode of Failure.

FIG. 9 shows an exemplary systems, apparatuses and methods by which data from various sources about a particular tree will be used to calculate and estimate various tree parameters and/or physical parameters to generate one or more outputs. Several inputs are analyzed to provide a range of values that can be used to model non-obvious relationships and parameters, which in turn can be used to calculate specific properties of a tree in its environment. As shown in 901, measurements from various sources can be used to calculate factors related to interactions between a tree and the external loads acting on it. As shown in 902, measurements can be used to evaluate the volume of the economic products that can be harvested from the tree. As shown in 903, parameters involved in stem failure due to breaking can be determined, while 904 shows factors that can be used to compute the risk of overthrow. As explained above, external data can be provided by third parties, such as weather services or commissioned soil reports. Lookup information sources can include data or algorithms found in libraries, such as calculations of root depth or other non-visible parameters based on features such as tree variety and stem measurements.

The tree parameters can then be used to determine one or more physical properties. For example, as shown in 905, several measures of the value of the tree, both economic and environmental, can be calculated. As shown in 906-908, the tree parameters can be used to calculate how the tree is predicted to fail if subjected to extreme environmental forces.

The embodiments described in this disclosure can be combined in various ways. Any aspect or feature that is described for one embodiment can be incorporated into any other embodiment mentioned in this disclosure. Moreover, any of the embodiments described herein may be hardware-based, software-based and/or comprise a mixture of both hardware and software elements. Accordingly, while various novel features of the inventive principles have been shown, described and pointed out as applied to particular embodiments thereof, it should be understood that various omissions and substitutions and changes in the form and details of the systems and methods described and illustrated, may be made by those skilled in the art without departing from the spirit of the invention. Amongst other things, the steps of any described methods may be carried out in different orders in many cases where such may be appropriate. Those skilled in the art will recognize, based on the above disclosure and an understanding therefrom of the teachings of the inventive principles, that the particular hardware and devices that are part of the system described herein, and the general functionality provided by and incorporated therein, may vary in different embodiments of the inventive principles. Accordingly, the particular system components are for illustrative purposes to facilitate a full and complete understanding and appreciation of the various aspects and functionality of particular embodiments of the present principles as realized in system and method embodiments thereof. Those skilled in the art will appreciate that the inventive principles can be practiced in other than the described embodiments, which are presented for purposes of illustration and not limitation.

What is claimed is:

1. A system capable of predicting a risk of catastrophic failure for one or more trees based on a mechanistic model of physical characteristics of the one or more trees, the system comprising:
 a mobile sensing platform comprising one or more sensors for obtaining imaging data;
 a transport vehicle that transports the mobile sensing platform, wherein the transport vehicle facilitates transportation of the mobile sensing platform over an area comprising the one or more trees and enables the mobile sensing platform to analyze the one or more trees for conditions relating to catastrophic tree failure;
 a positioning sensor that calculates geographic coordinates of the positioning sensor and a location of the positioning sensor relative to a reference object as positioning data; and
 a processor configured to fuse the imaging data and the positioning data in order to predict the conditions for catastrophic tree failure;
 wherein:
  the one or more sensors for obtaining the imaging data include one or more LiDAR sensors;
  the imaging data generated by the one more LiDAR sensors is used to model a canopy and a trunk of a tree with centimeter level accuracy; and
  the catastrophic tree failure relates to stem breakage or overthrow of the tree and is predicted, at least in part, using the fused imaging data and positioning data.

2. The system of claim 1, wherein the one or more sensors further include at least one of: an RGB sensor, a multispectral imaging sensor, a hyperspectral imaging sensor, a soil composition sensor, an ultrasonic sensor, a sonar imaging sensor.

3. The system of claim 1, wherein the positioning sensor achieves centimeter level accuracy.

4. The system of claim 1, wherein the positioning sensor includes an inertial measurement unit that calculates a change in location and orientation relative to a former position and orientation of the positioning sensor based on measurements of the sensor's inertia or magnetic fields.

5. The system of claim 1, wherein the processor performs simultaneous localization and mapping using IMU and point cloud data to determine location and orientation in GPS denied environments.

6. The system of claim 1, wherein the mobile sensing platform generates an assembled point cloud and, wherein the processor is further configured to:
 calculate dimensional and morphological data based on the assembled point cloud, and
 predict the conditions for catastrophic tree failure based on the dimensional and morphological data.

7. The system of claim 6, wherein the processor is further configured to:
 determine a form and size of a tree's root system and soil plate extents using species-specific heuristics of the morphological data; and
 determine the tree's counter moment potential based on an estimated soil plate weight calculated from the form and size of the tree's root system.

8. The system of claim 1, further comprising a storage medium for storing the imaging data received by the mobile sensing platform and a transceiver for transmitting the imaging data, wherein the processor is configured to convert the imaging data received from the mobile sensing platform into a different format.

9. The system of claim 1, further comprising a static database for storing associations between plant varieties and spectral signatures, and a dynamic database for storing forecasts of weather conditions in a particular locality.

10. The system of claim 1, wherein the conditions for catastrophic tree failure are predicted based on characteristics associated with a tree's species, and wherein the characteristics associated with the tree's species comprise density, strength and/or allowable flexion.

11. The system of claim 10, wherein the tree's species is determined by comparing multispectral and/or hyperspectral imagery of the tree with a library of spectral signatures.

12. The system of claim 1, wherein the processor is configured to model a tree's stem horizontal profile at one or more heights above ground, wherein the model includes anomalies from a circular profile and eccentricities of a tree stem structure.

13. The system of claim 12, wherein the processor is configured to fuse the model of the tree's stem horizontal profile with strength measures associated with a tree's species, the strength measures comprising moisture content of wood, and stem damage.

14. The system of claim 13, wherein the model of the tree's stem horizontal profile is used to determine the conditions by which the tree's stem will withstand lateral, gravitational, and torsional loads without breaking.

15. The system of claim 1, wherein the mobile sensing platform generates an assembled point cloud, and wherein the processor is further configured to:
 determine a wind force applied to a tree, wherein the wind force is based on a wind speed, and
 determine whether additional trees are surrounding and obstructing the tree based on the assembled point cloud data.

16. The system of claim 15, further comprising a weather database of wind projections, and wherein the processor is configured to create a tree profile based on the assembled point cloud, the tree profile including cloud vertices associated with a canopy, stem and branches of a tree, and wherein the processor is further configured to:
 calculate forces applied at each location of the tree profile based on the wind projections, and based on contextual data related to the tree's environment, the contextual data including a number and position of additional trees surrounding and/or obstructing the tree.

17. The system of claim 1, wherein:
 the processor is further configured to determine a wind speed and a wind pressure applied to a tree, and the processor adjusts the wind pressure based on a degree to which the tree's canopy is streamlined; and
 the processor is further configured to calculate bending and moment forces applied to the tree's stem, and strain experienced by the stem based on a bending modulus, density of the tree, volume of the tree, anticipated surface area capable of holding ice or snow, and projections for snow fall and ice accumulation.

18. The system of claim 1, wherein:
 the processor is further configured to calculate a tree's ability to resist bending, moment, and torsional forces applied to the tree's stem, and a minimum wind speed that will cause the tree to fail, the failure being stem breakage or overthrow;
 the processor is further configured to calculate the tree's ability to resist bending and moment forces imparted by gravitational loads based on wind vectors and anticipated snow and ice accumulation predictions;

the processor is further configured to calculate the tree's ability to resist bending, moment and torsional forces applied to the tree's stem, and the tree's ability to resist moment imparted by gravitational loads, based on external deformations of the tree's shape;

the processor is further configured to determine an expected failure force as a minimum force that will cause a failure in the tree due to forces applied to the tree's stem or forces imparted by gravitational loads, and determining a wind speed that results in the expected failure force;

the processor is further configured to generate a user interface that graphically displays a critical wind speed for a plurality of trees, and wherein the user interface indicates which tree of the plurality of trees is most likely to fail; or the processor is further configured to determine a likelihood of the tree failing based on weather data that indicates a likelihood of wind speeds reaching the critical wind speed of the tree.

19. The system of claim 1, wherein:

the processor is further configured to determine an order by which a plurality of trees will fail based on their respective critical wind speeds;

the processor is further configured to recursively simulate a failure of a tree from the plurality of trees based on the order, and recursively updates the critical wind speeds of the remaining trees from the plurality of trees; and the processor is further configured to determine a time and a set of specific trees which, when harvested or culled, increase or preserve an economic value of a stand by reducing a risk of catastrophic loss.

20. The system of claim 1, wherein:

the processor is further configured to calculate a change in critical wind speed of a tree based on harvesting activities or catastrophic loss affecting the tree or surrounding trees;

the processor is further configured to determine a harvesting route based on the data retrieved by the positioning sensor, and based on avoiding obstacles and damage to the tree; or the processor is further configured to determine a disease vector moving through the one or more trees based on spectral data obtained from the mobile sensing platform.

21. The system of claim 1, wherein:

the processor is further configured to extract trunk diameter measurements from assembled point cloud data; and calculate how many usable board feet of lumber can be harvested based on the extracted trunk diameter measurements.

22. The system of claim 1, wherein:

the processor is configured to fuse the imaging data and the positioning data in order to predict the conditions for catastrophic tree failure without an application of physical loading forces being applied to the one or more trees.

* * * * *